(12) United States Patent
Liou

(10) Patent No.: US 6,334,771 B1
(45) Date of Patent: Jan. 1, 2002

(54) RAPID PALATAL EXPANDER

(76) Inventor: Eric Jein-Wein Liou, No. 199, Tun-Hwa North Rd., Taipei (TW)

(*) Notice: Subject to any disclaimer, the term of this patent is extended or adjusted under 35 U.S.C. 154(b) by 0 days.

(21) Appl. No.: 09/662,875

(22) Filed: Sep. 15, 2000

(51) Int. Cl.[7] .................................................. A61C 3/00
(52) U.S. Cl. ............................................. 433/7; 433/19
(58) Field of Search ........................................ 433/7, 19

(56) References Cited

U.S. PATENT DOCUMENTS

| | | | | |
|---|---|---|---|---|
| 4,348,179 A | * | 9/1982 | Nardella | 433/7 |
| 5,645,423 A | * | 7/1997 | Collins, Jr. | 433/19 |
| 5,775,898 A | * | 7/1998 | Schellino et al. | 433/7 |
| 5,964,588 A | * | 10/1999 | Cleary | 433/19 |
| 5,975,894 A | * | 11/1999 | Pozzi | 433/7 |

* cited by examiner

*Primary Examiner*—John J. Wilson
(74) *Attorney, Agent, or Firm*—Dougherty & Troxell

(57) ABSTRACT

A rapid palatal expander for stretching a patient's upper jaw bone sideward horizontally and forward to accommodate front teeth. It has a dual-joint jack screw with two rocker arms having respectively one end pivotally engaged with two spaced fulcrums and another end engageable with a screw bar. Turning the screw bar will move the rocker arm moving outward to push upper barrel bands mounted on the molar and premolar horizontal outward to expand the upper jaw bone. There is an elastic means with two ends engaged with the upper and lower barrel bands mounted respectively on the upper and lower molar and premolar. When patient's mouth is closed, the elastic means will be compressed to produce a horizontal force to push the upper barrel band forward. Thus the upper jaw bone and the teeth may also receive a constant forward pushing force for expanding purpose.

8 Claims, 5 Drawing Sheets

RAPID PALATAL EXPANDER

1. FIELD OF THE INVENTION

This invention relates to a palatal expander and particularly a dual-joint palatal expander to expand upper jaw bone effectively and quickly for accommodating and aligning the front teeth of a patient.

2. BACKGROUND OF THE INVENTION

Because of oral disorder or disease, there are cases in which patients, particularly children of young age, need surgical or plastic operation to cut through the palatal or upper jaw bone and gum. After surgical operation, the upper jaw bone need to be expanded for accommodating and aligning the front teeth. Hence a palatal expander is usually employed to expand the upper jaw bone sideward and forward to create more space for the front teeth to grow and align properly.

FIG 1 shows a conventional palatal expander 6 which is also known as jackscrew mounted in the upper jaw of the patient. It has a pair of spaced anchor blocks 62 which have respectively an opposite internal screw bore engageable with a screw bar 64. The anchor blocks 62 are slidable movable along two spaced guide rods 63 which run through the anchor blocks 62. Each anchor block 62 has one side attached to a pair of brackets 61 which have one end fastened to a first upper barrel band 11 and a second upper barrel band 21. The first and second barrel bands 11 and 21 are mounted respectively on a molar 1 and a premolar 2. There is a wire anchor 30 on each barrel band and a steel wire 3 to fasten the first and second barrel bands 11 and 21 together. Turning a screw head 641 located between the anchor blocks 62, the screw bar 64 will be turned and drives the anchor blocks 62 away from each other. The brackets 61 will then push the barrel bands 11 and 21 of two sides away from each other. As the molar 1 and premolar 2 have relatively strong root deeply planted in the upper jaw bone, the upper jaw bone will be stretched and expanded. FIG. 2 shows what is actually happening when using the jackscrew 6 shown in FIG. 1. The upper jaw bone at the front teeth position will be stretched in two opposite directions A and B sideward and slightly backward against a center O and forming a fan angle $\alpha$. The stretch direction A and B is not linear. Instead of expanding the upper jaw bone sideward and forward, the upper jaw bone will be expanded sideward but crowed backward. The direction of front teeth expansion is unpredictable. This will cause the misalignment of the front teeth. Then an orthodontic treatment is needed to align the front teeth. This adds more pain and trouble to the patients.

FIG 3 shows another conventional palatal expander 6' also known as a fan-type jackscrew. The operation principle is generally same as the one shown in FIG. 1. However instead of a pair of anchor blocks 62 and guide rods 63, a pair of rocker arms 65 are used to engage with the screw bar 64'. Each rocker arm 65 has a screw end 642 engaged with the screw bar 64' and a pivotal center 66 engaged with another rocker arm 65. Turning the screw head 641', the screw bar 64' will turn and drive the screw end 642 away from each other. Then the rocker arms 65 will be expanded to a wider angle about the pivotal center 66 to move the bracket 61 to push the barrel bands 11 and 21. As a result, the upper jaw bone may also be expanded. The expanding direction A' and B' (shown in FIG. 4) is also being stretched slightly backward against a center O' and forming a fan angle $\alpha'$. It also has similar disadvantage shown in the FIG. 1 example.

Furthermore the prior arts set forth above are difficult to install and use. It is particularly troublesome for children who generally have not much patience to endure such an ordeal for a long period of time. Most children have great resistance to take this long and painful treatment. Even to those children who take this treatment, the effectiveness will be compromised when proper adjustment is not performed regularly. The treatment takes long time and great cost. All this begs for improvement.

SUMMARY OF THE INVENTION

It is an object of this invention to provide a rapid palatal expander that is able to expand upper jaw bone of a patient sideward and forward almost linearly so that the upper jaw bone will be stretched horizontally and forward to accommodate the front teeth and growing alignment.

It is another object of this invention to provide a rapid palatal expander that can expand upper jaw bone of a patient effectively and quickly so that total treatment time may be shortened to relieve patient's trouble and inconvenience and to reduce expense.

It is a further object of this invention to provide a rapid palatal expander that has a constant expansion feature that enables the upper jaw bone of a patient be stretched as desired constantly and automatically without patient's active involvement or extra efforts. It may further speed up total treatment time and save medical expense.

In one aspect, the palatal expander according to this invention includes a dual-joint fan-type jackscrew. A pair of rocker arms each has one end respectively engaged with a fulcrum and another end engageable with a screw bar. Turning the screw bar, the rocker arms will be moved away sideward in opposite direction to stretch the upper jaw bone sideward and forward. The two fulcrums may be spaced from each other to enable the sideward movement of the rocker arms become almost a linear path. The backward stretching that happened to a single joint fan-type jackscrew thus may be minimized.

In another aspect, this invention provides an elastic means which has two ends engageable with molars of the upper and lower jaw. When patients mouth is closed, the elastic means will be compressed by the upper and lower jaw and produces a forward force to push the upper jaw bone forward.

This may be done without patient's additional effort, during day time and even in sleep. The jaw bone expanding effect is thus greatly enhanced. It may further shorten total treatment time and may also save the patient a lot of trouble and medical expense.

BRIEF DESCRIPTION OF THE DRAWING

The invention, as well as its many advantages, may be further understood by the following detailed description and drawings in-which.

DETAILED DESCRIPTION OF THE PREFERRED EMBODIMENT

Figure 1:
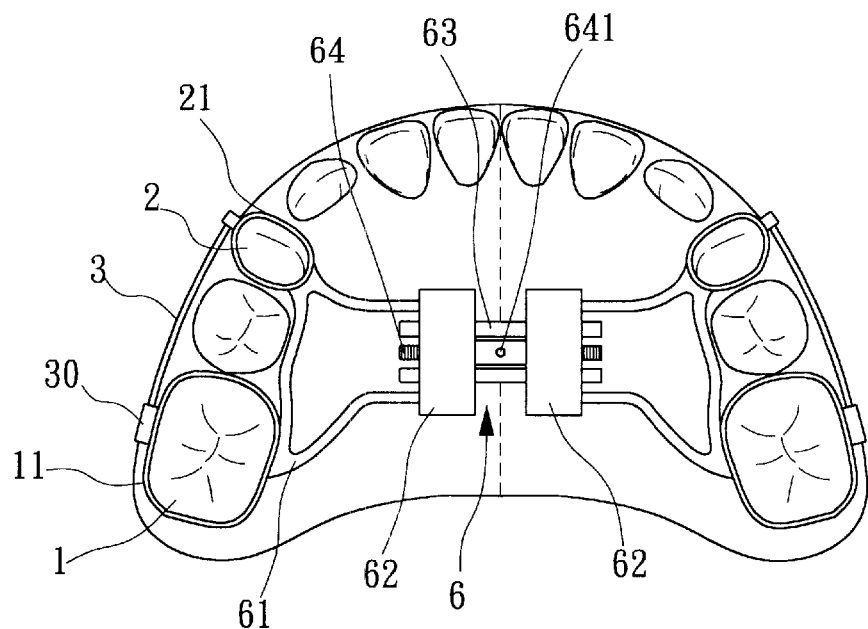
FIG. 1 illustrates a conventional jackscrew type palatal expander.
Figure 2:
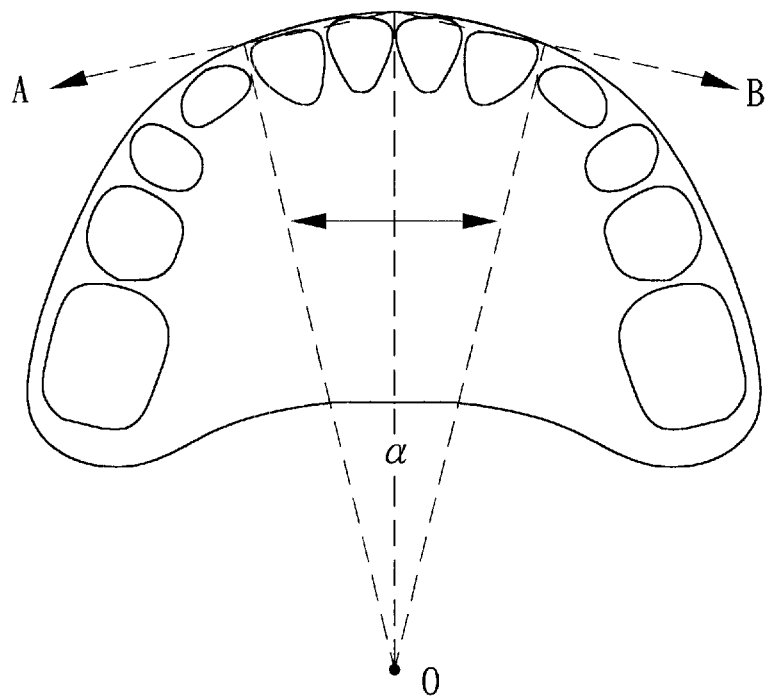
FIG. 2 is a diagram of treatment effect by using the palatal expander shown in FIG. 1.
Figure 3:
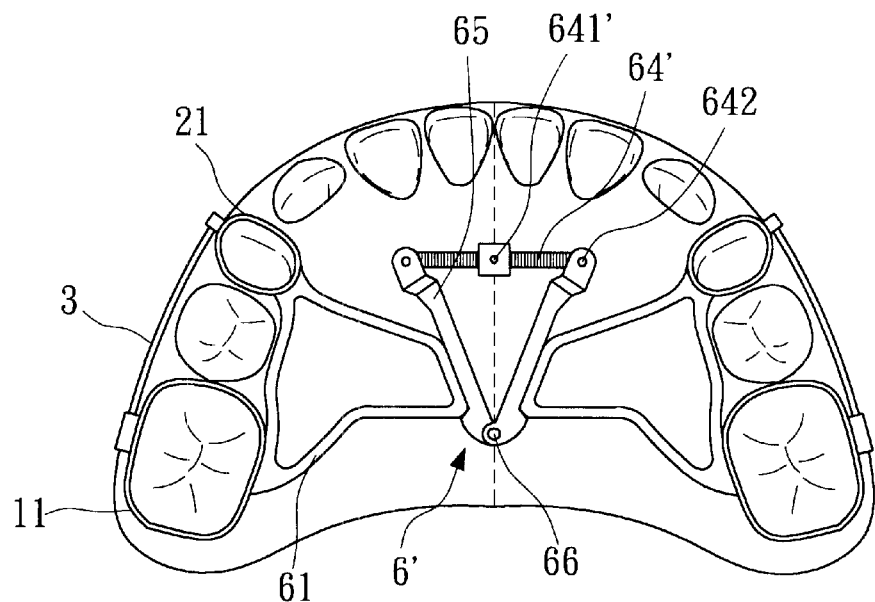
FIG. 3 illustrates another conventional fan-type jackscrew palatal expander.
Figure 4:
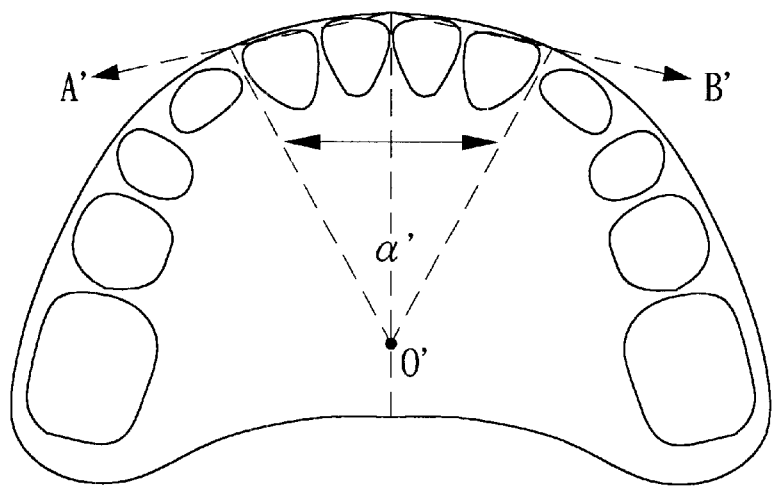
FIG. 4 is a diagram of treatment effect by using the palatal expander shown in FIG. 3.
Figure 5:
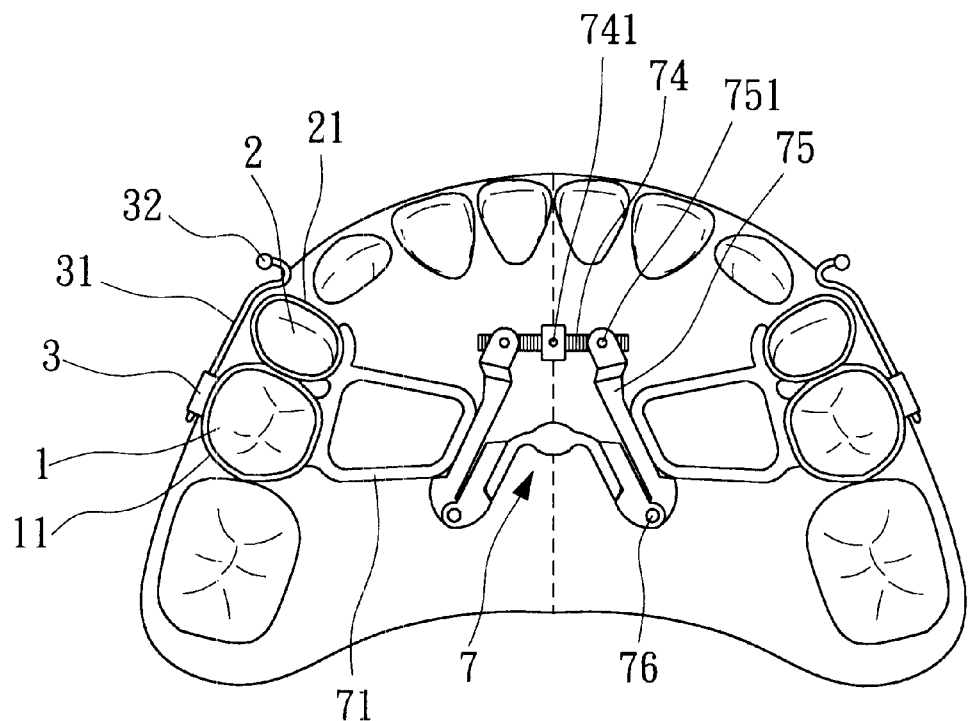
FIG. 5 shows a preferred embodiment of this invention being mounted on the teeth.
Figure 8:
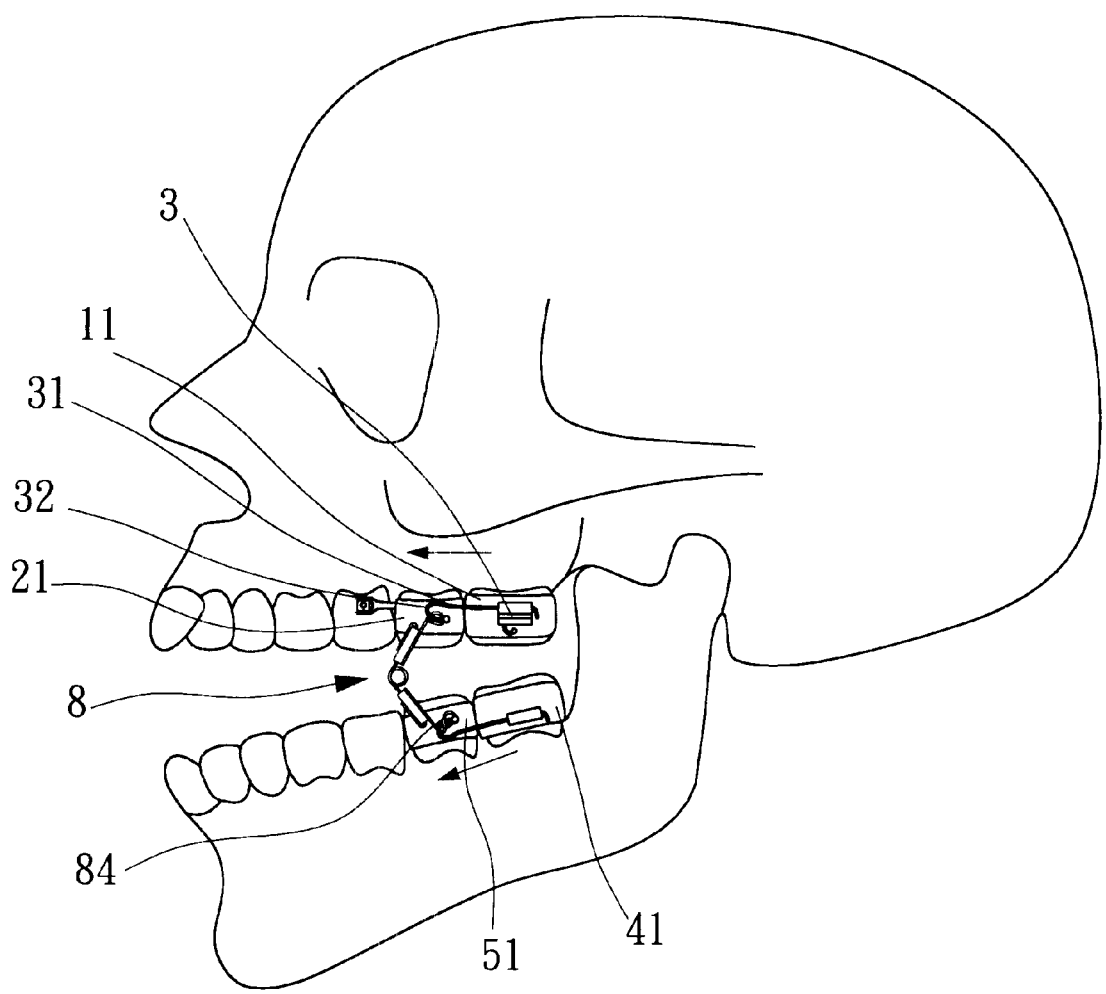
FIG. 8 is a pictorial view of this invention in use.

Referring to FIGS. 5 and 8, the palatal expander according to this invention includes a dual-joint fan-type jackscrew, an elastic means 8, at least one upper barrel band 11 and at least one lower barrel band 41.

The jackscrew 7 includes two rocker arms 75. Each rocker arm has one end pivotally engaged with a fulcrum 76 and the other end engaged with a screw end 751 which has an internal screw threads formed therein. The two fulcrums 76 are spaced from each other. The internal screw threads in the two screw end 751 are opposite to each other.

There is a screw bar 74 which has two ends engageable with the internal screw threads at the screw end 751 of the rocker arms 75. A screw head 741 is provided in the middle of the screw bar 74. The rocker arm 75 has a side wall attached to one end of a bracket 71. The bracket 71 has another end fastened to the upper barrel bands 11 and 21. In FIG. 5, two upper barrel bands 11 and 21 are mounted respectively on a molar 1 and a premolar 2 at each side of the mouth. On the side wall of the upper barrel band 11, a wire anchor 3 is provided. There is a steel wire 31 which has one end fastened to the wire anchor 3 and another end shaped like a hook 32.

The lower jaw also has two barrel bands 41 and 51 mounted respectively on a molar and premolar in the lower jaw and a steel wire which also has one end fastened to the barrel band and another end shaped like a hook (unmarked in FIG. 8).

Figure 7:
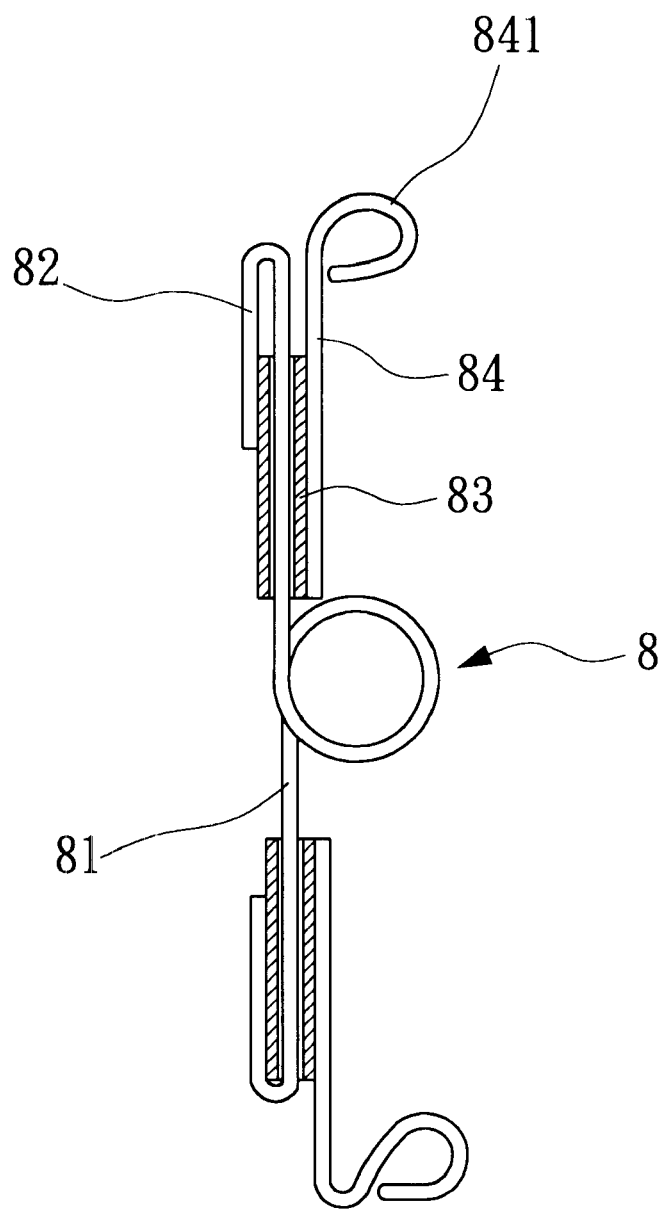
FIG. 7 is a sectional view of an elastic means for this invention.

Referring to FIGS. 7 and 8, the elastic means 8 includes a torsional wire spring with two wire arms 81 stretched in opposite directions. The end of each arms 81 is bent to form a stopper 82. There is a sleeve 83 slidable on the arm 81 without slipping out of the stopper 82. There is a latch wire 84 fixed on the sleeve 83. The latch wire 84 has one end formed like an ear 841. When there is no external force being applied on the elastic means 8, the angle between the two wire arms 81 is greater than 90°, preferably between 120°~180°. Such that a horizontal pushing force will be provided by the wire arms 81 when they are compressed toward each other. If the angle between these two wire arms 81 is less than 120° (or even smaller than 90°), a relatively greater force will occur in a vertical direction but not horizontal.

When in use, at least one barrel band is mounted respectively on the upper and lower jaw at each side. In the embodiment shown in FIGS. 5 and 8, the upper barrel band 11 is mounted on an upper molar 1, the upper barrel band 21 is mounted on an upper premolar 2, the lower barrel bands 41 and 51 are respectively mounted on a lower molar and lower premolar. Each pair of barrel bands located at the upper and lower jaw attach a wire anchor 3. The steel wire 31 is fastened to the wire anchor 3 and has the hook 32 engaged with the ear 841 of the elastic means 8.

Figure 6:
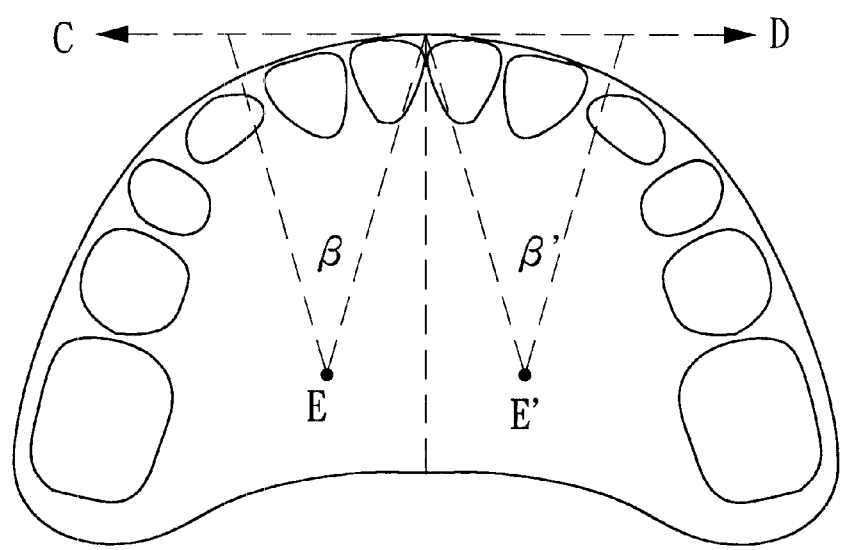
FIG. 6 is a diagram of treatment effect by using this invention shown in FIG. 5.

To perform the palatal expansion, the screw head 741 is turned to make the screw end 751 moving outward in opposite direction (shown by C and D in FIG. 6). The rocker arm 75 will turn about the fulcrum 76 at an angle β (or β') (shown in FIG. 6, in which points E and E' coincide the two fulcrums 76 in FIG. 5). The two fulcrums 76 may be so spaced as to make the screw end 751 moving displacement almost linear sideward without backward stretching. Hence upper jaw bone may be stretched sideward with desirable result without backward crowding. The direction of front teeth expansion can be well controlled.

Moreover, when the patient closes the month, the elastic means 8 will ,0 be compressed and bent in the front direction (shown in FIG. 8). Then a torsional spring force will drag the hook 32 through the ear 841 to force the upper barrel bands 11 and 21 moving forward which in turn moves the upper jaw bone together with the teeth forward. The sideward and forward stretching of the upper jaw bone then may gradually expand the palatal to meet desired purpose.

The turning of the screw head 741 may be easily done by a simple hand tool. As a turn or a fraction of a turn of the screw bar 74 will make a constant sideward displacement for the screw end 751, it may even be done under dentists direction at home without visiting dentist clinic. The elastic means 8 will produce a horizontal and forward force to push the upper jaw bone and the teeth whenever patient's mouth is closed. The treatment is effective in day time or during sleep. The forward pushing force is thus constantly applied without additional or extra work from the patient. It is more effective and may greatly shorten treatment time. Total medical expenses may also be reduced.

It may thus be seen that the objects of the present invention set forth herein, as well as those made apparent from the foregoing description, are efficiently attained. While the preferred embodiment of the invention has been set forth for purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A rapid palatal expander configured to be mounted in a patient's jaw for enlarging an upper jaw bone sideward and forward, comprising:

at least one upper barrel band adapted to be mounted on an upper molar having an upper anchor located thereon;

at least one lower barrel band adapted to be mounted on a lower molar having a lower anchor located thereon;

an elastic device having two ends engageable respectively with the upper and lower anchors, the elastic device including a torsional spring, the torsional spring including two arms extending in opposite directions, each arm having one end formed as a stopper and a sleeve movable thereon, the sleeve having a latch wire with one end formed with an ear engaging one of the anchors; and a dual-joint jackscrew having a pair of spaced rocker arms, a screw bar turnable by a screw head and two brackets each bridged between the rocker arm and the upper barrel band, the rocker arms each having one end pivotally engaged with one of a pair of spaced apart fulcrums and a screw end having an internal screw thread engaging the screw bar;

wherein upon turning the screw head, the screw bar will be turned to move the screw end outward for a selected displacement so that the rocker arms will move the brackets to push the barrel band outward and upon the patient closing the mouth, the elastic device will be compressed to produce a horizontal forward force on the upper barrel band.

2. The rapid palatal expander of claim 1, wherein the upper anchor includes a wire anchor fixed on a side of the barrel band and a steel wire having one end formed in a hook and engaging the elastic device.

3. The rapid palatal expander of claim 1, wherein the lower anchor includes a wire anchor fixed on a side of the barrel band and a steel wire having one end formed in a hook and engaging the elastic device.

4. The rapid palatal expander of claim 1, wherein the internal screw threads of the two screw ends are opposite to each other.

5. The rapid palatal expander of claim 1, wherein two upper barrel bands are provided and are configured to be mounted respectively on an upper molar and an upper premolar.

6. The rapid palatal expander of claim 1, wherein two lower barrel bands are provided and are configured to be mounted respectively on a lower molar and a lower premolar.

7. The rapid palatal expander of claim 1, wherein each bracket has two spaced beams bridged between the rocker arm and the upper barrel bands.

8. The rapid palatal expander of claim 1, wherein the pair of fulcrums are spaced apart such that they are located substantially on a horizontal linear line.

* * * * *